United States Patent [19]
Astle

[11] Patent Number: 5,525,302
[45] Date of Patent: Jun. 11, 1996

[54] METHOD AND DEVICE FOR SIMULTANEOUSLY TRANSFERRING PLURAL SAMPLES

[76] Inventor: Thomas W. Astle, 607 Harborview Rd., Orange, Conn. 06477

[21] Appl. No.: 649,431

[22] Filed: Feb. 1, 1991

[51] Int. Cl.$^6$ .................................................. B01L 3/02
[52] U.S. Cl. ........................... 422/100; 422/67; 436/49; 436/54; 436/180; 73/864.12; 73/864.13; 73/864.15; 73/864.35
[58] Field of Search ................... 422/100, 67; 436/49, 436/54, 180; 73/864.12, 864.13, 864.15, 864.16, 864.22, 864.35; 222/309

[56] References Cited

U.S. PATENT DOCUMENTS

| | | | |
|---|---|---|---|
| 2,984,391 | 5/1961 | Watters et al. | 222/309 |
| 3,568,735 | 3/1971 | Lancaster | 141/238 |
| 3,712,794 | 1/1973 | Fan | 422/100 |
| 3,830,108 | 8/1974 | Spong | 73/864.16 |
| 4,148,859 | 4/1979 | Simpson et al. | 422/100 |
| 4,294,802 | 10/1981 | Johansson | 422/100 |
| 4,302,421 | 11/1981 | Baker | 73/864.16 |
| 4,399,711 | 8/1983 | Klein | 422/100 |
| 4,459,864 | 7/1984 | Cirincione | 422/100 |
| 4,555,957 | 12/1985 | Frankel | 73/864.16 |
| 4,562,871 | 1/1986 | Astle | 141/129 |
| 4,565,100 | 1/1986 | Malinoff | 422/100 |
| 4,824,642 | 4/1989 | Lyman et al. | 422/100 |
| 5,021,217 | 6/1991 | Oshikubo | 422/100 |
| 5,055,408 | 10/1991 | Higo et al. | 436/49 |
| 5,104,621 | 4/1992 | Pfost | 422/100 |

OTHER PUBLICATIONS

"Pipettor/Mixer Dispenser/Diluter" brochure by Soken, Gardena, California Date unknown, but predates Applicant's invention.

"What's New From Zymark!!" brochure by Zymark, Hopkinton, Massachusetts Date unknown, but predates Applicant's invention.

"A randon access EIA system based on magnetic microbead technology" reprinted by TECAN US, Hillsborough, North Carolina, Mar. 1990.

"The Microlab 2200" brochure by Hamilton Company, Reno, Nevada, 1988.

"Microlab AT" brochure by Hamilton Company, Reno, Nevada. Date unkown but predates Applicant's invention.

Primary Examiner—Robert J. Warden
Assistant Examiner—Jan M. Ludlow
Attorney, Agent, or Firm—John H. Crozier

[57] ABSTRACT

In a preferred embodiment, a multiple sample transfer device which includes a plurality of hollow pistons disposed in a like number of cylindrical channels and connected to a moving plate to permit simultaneous movement of the pistons. At the lower end of each channel is a removable pipette tip. An apparatus is provided to bring a multiwell sample tray into operating engagement with the pipette tips. Flexible tubes are attached between the upper ends of the hollow pistons and a liquid reservoir. Clamping devices are provided to permit the selective pinching or opening of the tubes. When the tubes are pinched, the pistons can be used in either liquid-back-filled or air displacement modes to aspirate and dispense liquids from and to the sample tray. When the tubes are selectively sequentially pinched or open, aspiration and dispensing can be controlled by the timing of the pinching and the provision of vacuum or pressure in the liquid reservoir. All operations, including mounting and removal of the pipette tips, can be automatically controlled through use of a programmable computer.

10 Claims, 8 Drawing Sheets

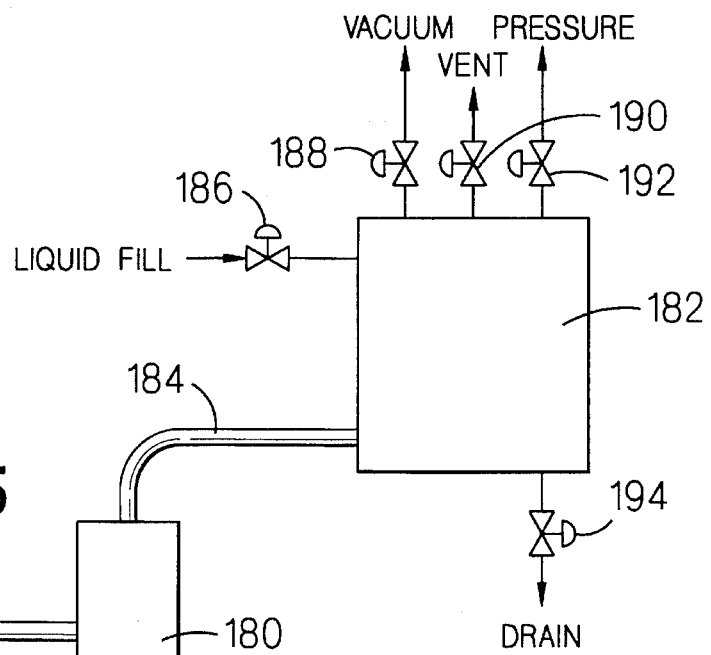
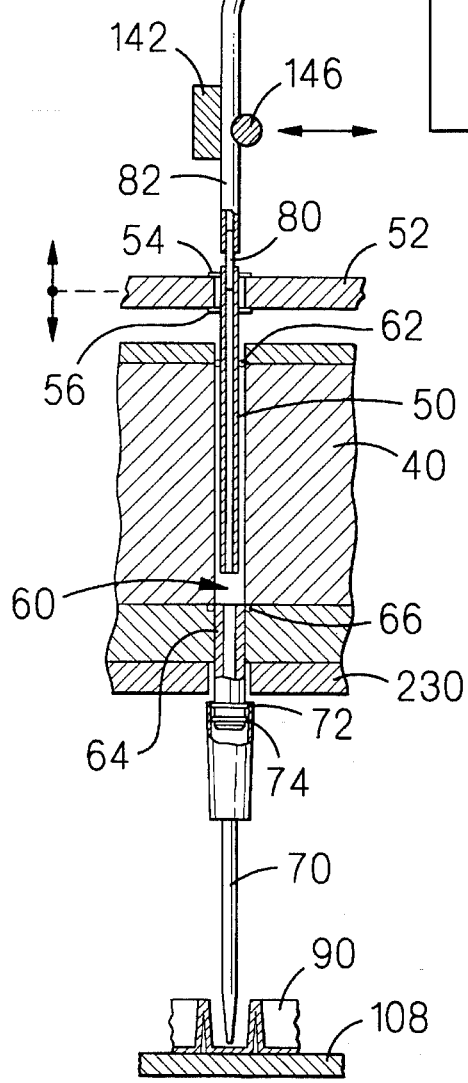
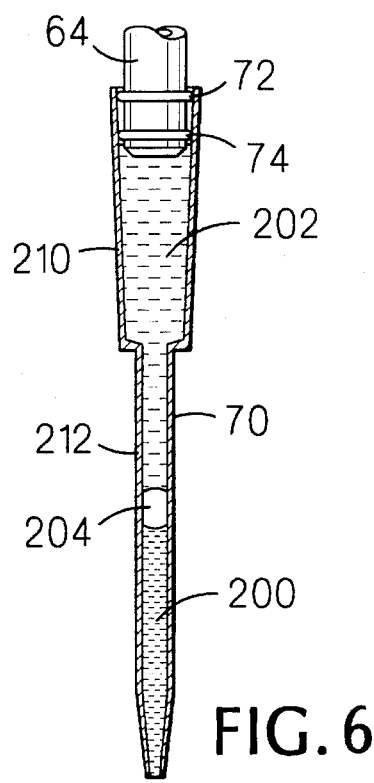
FIG. 5
FIG. 6

METHOD AND DEVICE FOR SIMULTANEOUSLY TRANSFERRING PLURAL SAMPLES

BACKGROUND OF THE INVENTION

1. Background Art

The present invention relates generally to sample transfer systems and, more particularly, to a novel sample transfer system which employs a plurality of pipettes to transfer simultaneously samples between welled trays.

2. Background Art

One of the primary requirements in laboratory research, especially in the biotechnology and medical fields, is to transfer small aliquots of various liquids from one container to another. Such transfers may be made through the use of individual or multiple pipettes. As the sensitivity of the testing protocols has been increased, the volume of reagents and samples has been reduced to microliter quantities. Today, the de facto standard for biotechnological and medical research fields is a 96-well protocol using an array of small wells in a thermoplastic tray. The wells, holding up to 300 microliters per well, are usually arranged in an 8×12 matrix on 9-mm centers.

Typically, the user pipettes the sample or reagent volumes into these wells. Individual volumes range from 1 microliter up to the 300 microliters required to fill the volume of the well. For those protocols that require higher volumes, a deep well container is used in which each well holds 1 to 2 ml. These deep wells may be individual tubes or they may be formed as a molded unit. However, they are also usually arranged in the standard 8×12 matrix on 9-mm centers to take advantage of the variety of automated and manual devices that have been developed around this standard.

The sample transfer devices range from individual manual pipettes to multiple pipettors handling a row of 8 or 12 samples at a time. The manual devices have been augmented by automated devices that process complete sets of 96 samples by indexing the sample plate one row at a time under the pipetting device. Robotic arm assemblies and X-Y-Z bridge assemblies have added further automation and flexibility of processing. However, even the latter are relatively slow, in that not all wells are serviced simultaneously.

The necessity of preventing cross-contamination between samples has led to the use disposable tips on the end of the pipettor assemblies. Packaging has allowed these tips to be loaded individually or in rows of 8 or 12 using manual or automatic means. Generally, the tips are held to the pipettors with a tapered friction fit that (1) seals the connection, and (2) allows the tip to be ejected manually or automatically, though some employ a double O-ring arrangement that both seals and holds the tips in proper orientation. The latter do not provide means for automatic tip ejection.

The testing protocol's sensitivity has placed increased importance on the accuracy of the liquid transfer device. Most pipetting devices today use an air displacement method of aspirating or dispensing liquid. The newer devices use positive displacement, minimizing the volume of any compressible fluid, such as air between the sample and the displacement plunger or device.

These advances in the technology make it economical to process a higher number of samples. However, each new level of testing encounters some area of resistance to the desired higher throughput. Presently, the limiting factor is reading endpoints on pipettes. However, new developments are being developed to quickly and economically read 96 samples with colorimetric or radiometric means. With these advances, the throughput limitation becomes sample preparation and processing. No known transfer device provides for the selective use of either air displacement or positive displacement liquid transfer methods with a single apparatus. None provides for fully programmable sequencing of tip insertion, liquid transfer, and tip ejection.

Accordingly, it is a principal object of the present invention to provide method and means for the simultaneous transfer of a plurality of liquid samples which method and means employs a device which provides for the selective use of either air displacement or positive displacement liquid transfer.

It is a further object of the invention to provide such method and means which can be programmed for the sequence of tip insertion, liquid transfer, and tip ejection.

It is another object of the invention to provide method and means for the simultaneous mounting of a plurality of tips to a pipetting device.

It is an additional object of the invention to provide method and means for the simultaneous ejection of a plurality of tips from a pipetting device.

A further object of the invention is to provide the foregoing methods and means which are economically constructed and used.

Other objects of the present invention, as well as particular features, elements, and advantages thereof, will be elucidated in, or be apparent from, the following description and the accompanying drawing figures.

SUMMARY OF THE INVENTION

The present invention accomplishes the above objects, among others, by providing, in a preferred embodiment, a multiple sample transfer device which includes a plurality of hollow pistons disposed in a like number of cylindrical channels and connected to a moving plate to permit simultaneous movement of the pistons. At the lower end of each channel is a removable pipette tip. An apparatus is provided to bring a multiwell sample tray into operating engagement with the pipette tips. Flexible tubes are attached between the upper ends of the hollow pistons and a liquid reservoir. Clamping means are provided to permit the selective pinching or opening of the tubes. When the tubes are pinched, the pistons can be used in either liquid-backfilled or air displacement modes to aspirate and dispense liquids from and to the sample tray. When the tubes are selectively sequentially pinched or open, aspiration and dispensing can be controlled by the timing of the pinching and the provision of vacuum or pressure in the liquid reservoir. All operations, including mounting and removal of the pipette tips, can be automatically controlled through use of a programmable computer.

The basic element of the instrument is the head. It consists of a block of material into which 96 cavities are machined. Within each cavity, a separate piston moves to create a displacement. All 96 pistons are connected to a common driving element. This driving element is positioned and controlled through electronic and electromechanical means. In the basic device, this is a computer controlled stepper motor, or a servo motor driving a lead screw that moves the piston assembly in and out of the cavities.

Each piston is sealed to its cavity sidewall by elastomeric means. This may be one or more "O" rings, or a lip type seal, with a garter spring. As the piston moves, it creates a displacement with respect to the end of the opening. One end is connected with a sealing means to the dispensing tip. The other end is open to the atmosphere to prevent back pressure effects. The net result is that, as the piston moves, fluid may be aspirated or dispensed through the tip opening.

In many applications, it is sufficient to wash the sample handling tip between samples to prevent carry-over. This invention describes two ways in which this may be accomplished. In the first, and most simple method, a port is exposed in each piston cavity when the piston driving head is at its uppermost extreme position. This port communicates with a manifold assembly connecting all ports to a common fluid line. With the pistons up, the ports are open, and flushing fluid, under some external driving means (pressure), flows through the cavity and out the tip, cleaning this internal passageway. The exterior of the tip may be concurrently washed from the outside by inserting it in a washing bath.

The second means of washing the tip provides an additional useful feature. In many dispensing applications, the precision of a displacement system is not required. The second method of this invention combines a time pressure delivery method with that of the displacement method. Each position is connected to a fluid source by means of an individual elastomeric tube. A clamp is provided to pinch these tubes closed. With the clamp closed, all tubes are pinched shut which, in effect, closes the bore of each piston. As the piston moves within its cavity, it displaces fluid ahead of it, allowing the discharge tip to aspirate and dispense.

With the clamp open, all piston cavities are connected to the fluid source on the opposite side of the clamp. Pressurizing this fluid source will cause fluid to be expelled through the elastomeric tubes, through the piston cavity, and through the dispensing tip orifice. Controlling the length of time the clamp is open and the driving pressure on the fluid provides means of controlling the amount dispensed.

Allowing the use of back entry of fluid through the pistons, greatly increases the usefulness of the design. As described above, it allows the entry of a washing fluid to rinse the internal passageways. Secondly, it allows two fluids to be dispensed through the same tip orifice. One is aspirated up from an external source into the tip, and then expelled with the second fluid through the piston. In this case, a means separate from the piston head movement would be used to open and close the clamp tubes.

The use of back entry of fluid allows the system to become a positive displacement system. The displacement action of the piston may be accomplished with an incompressible fluid, such as water, as opposed to a compressible fluid such as air.

For many applications the only sure way of preventing cross contamination is to use a separate liquid handling surface for each sample. Other applications can tolerate washing the liquid handling surfaces. This invention utilizes a special molded tip as the liquid handling surface. The fact that 96 tips must be loaded simultaneously adds complexity to the problem. The force required to use a tapered press fit on 96 tips simultaneously would be excessive, and it would require extremely tight manufacturing tolerances. This invention uses two elastomeric "O" rings to seal and position each tip less force is required to effect the seal using an "O" ring. The second "O" ring is spaced apart from the first. While it does also seal, its primary purpose is to hold the tip in alignment.

A set of fingers is mounted between the piston head block and the "O" rings. Forcing these fingers down into contact with the top surface of the tips, strips them from the "O" ring mounting.

The maximum volume of a standard 96-well plate is 300 microliters per well. Thus, it is desirable to have the tip hold a volume in excess of 300 microliters. 500 microliters has been chosen as the tip volume. However, the tip must be able to aspirate and accurately dispense any volume within its range. In addition, it must be able to reach the bottom of the new deep well plates or sample tubes. The tip design used in the present invention accomplishes this. It consists of a narrow extended tip lower portion connected to a wider upper body. The upper body is designed to accommodate the sealing "O" rings. A step between the upper body and the extended tip provides a reference point for loading and handling the tip. This step surface supports the tips while they are inserted onto the tips. This provides a reference length between the head and the step which is also referenced to the tip end. This allows the tips to be loaded automatically, and still maintain a fixed known dimension for the location of the end of the tips. This is essential, since in delivering small microliter quantities (i.e., 1 to 5 microliters) it is necessary to touch off the end of the tip against the side of the well to release the drop.

Since the tip must be disposable, it must also be low cost. The tip used in the present invention is designed to be molded from many low cost thermoplastics using a conventional injection molding process. However, on some applications, additional cost can be justified if the tip can be washed out between uses, thereby allowing re-use. To enable this washing, various fillers may be used to decrease the tip surface's wettability. Normally, due to cost and its inert character, polypropylene, or its derivatives, is the resin of choice. By adding tetrafluoroethylene compounds to the basic polyolefin resin, a more inert tip may be obtained, one that is less wettable by aqueous solutions, and thus will carry over less.

The mechanics of the system described above are essential for its operation. However, the actual operation is a function of the control system used to drive it. The control system must provide the functional control and ease of use by the operator. The functional control consists of the following. The head driving the pistons must be precisely position controlled. This may be done with a number of well-known means. A stepper motor system may be used to drive a leadscrew, thereby converting controlled rotational movements to linear motion. The stepper motor may be replaced with a servo motor system using position feedback. The position feedback may come from a rotary encoder or a linear transducer direct connected to piston travel.

The speed of piston travel is an important factor. To deliver precise quantities of liquid from the tip orifice, the velocity of the liquid stream and its associated kinetic energy must exceed the surface tension forces at the tip orifice. If not, the tip delivery will be as drops, with surface tension controlling the size of the drop, and thus the delivery volume, and not the measured displacement that was desired. The speed of delivery should be a function of delivery volume. If the speed is too fast, the stream will have too much energy and bounce or splash from its intended receptacle.

The ease of use allows the operator to pre-set programs to create various aspirate and dispense protocols. Separate programs are required, since the instrument may be used by any one user for many applications. Each program is user set to control several aspirate and dispense cycles, each with its prescribed volume of transfer. The user may then select the desired program at time of use. Typical programs may be as follows;

Application: Make Mother/Daughter Plates:
 500 microliters are aspirated from one set of samples and then dispensed in 10 microliter quantities to 50 daughter plates Application: Add Several Reagents to Each Well:
 Aspirate 25 microliters of Reagent A
 Aspirate 5 microliters Air Gap to Separate Reagents
 Aspirate 50 microliters of Reagent B
 Aspirate 5 microliters of Air Gap
 Aspirate 25 microliters of Reagent C
 Dispense Contents into the Well
 Complete a series of 250 microliter Aspirate and
 Dispensing cycles to mix the contents of the well
 Final Dispense to clear Tip The flexibility of operation provided by the control system must be equalled by the flexibility of presenting various containers and devices from and to which to aspirate and dispense. In a complex automated system, the various sample plates and reagent reservoirs are positioned automatically by mechanized infeed-outfeed devices.

In a manual system, the stage, or plate carriage, is an X-Y platform that is moved manually by the operator. It allows six separate devices to be positioned below the aspirate-dispense head. One station is used for tip loading. Another station is used for tip removal. One station holds the sample container, leaving three stations to hold reagent reservoirs. Only the tip loading and tip removal stations are committed stations. The other four are identical and could be used in many combinations depending on operator needs.

BRIEF DESCRIPTION OF THE DRAWING

Understanding of the present invention and the various aspects thereof will be facilitated by reference to the accompanying drawing figures, submitted for purposes of illustration only and not intended to define the scope of the present invention, in which:

FIG. 5 is a side elevational view, partially in cross-section and partially schematic, of a single fluid path of the device of FIG. 1.

FIG. 6 is an enlarged side elevational view, partially in cross-section, of a tip for use with the present invention, with liquid therein.

DETAILED DESCRIPTION OF THE PREFERRED EMBODIMENTS

Figure 1A:
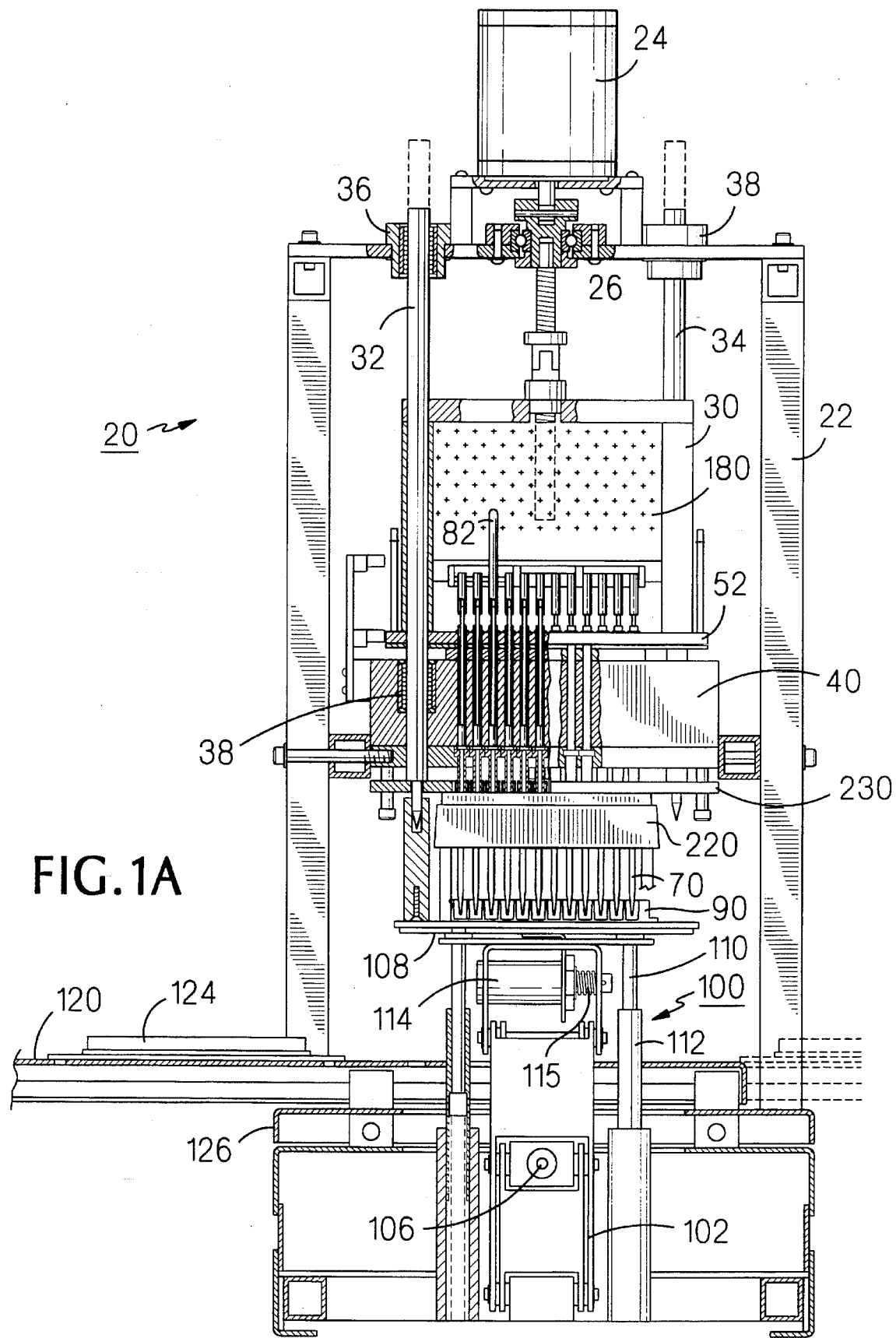
FIG. 1A is a side elevational view, partially in cross-section, partially cut-away, and partially schematic, of an automatic sample transfer device according to the present invention.

Referring now to the Drawing, provided for illustrative purposes only and not intended as a limitation on the invention disclosed herein, similar or identical elements are given consistent identifying numerals throughout the various figures thereof and parenthetical references to figure numbers direct the reader to the view(s) in which the element(s) being described is (are) best or alternatively seen, although the element(s) may be seen also in other views.

Figure 1B:
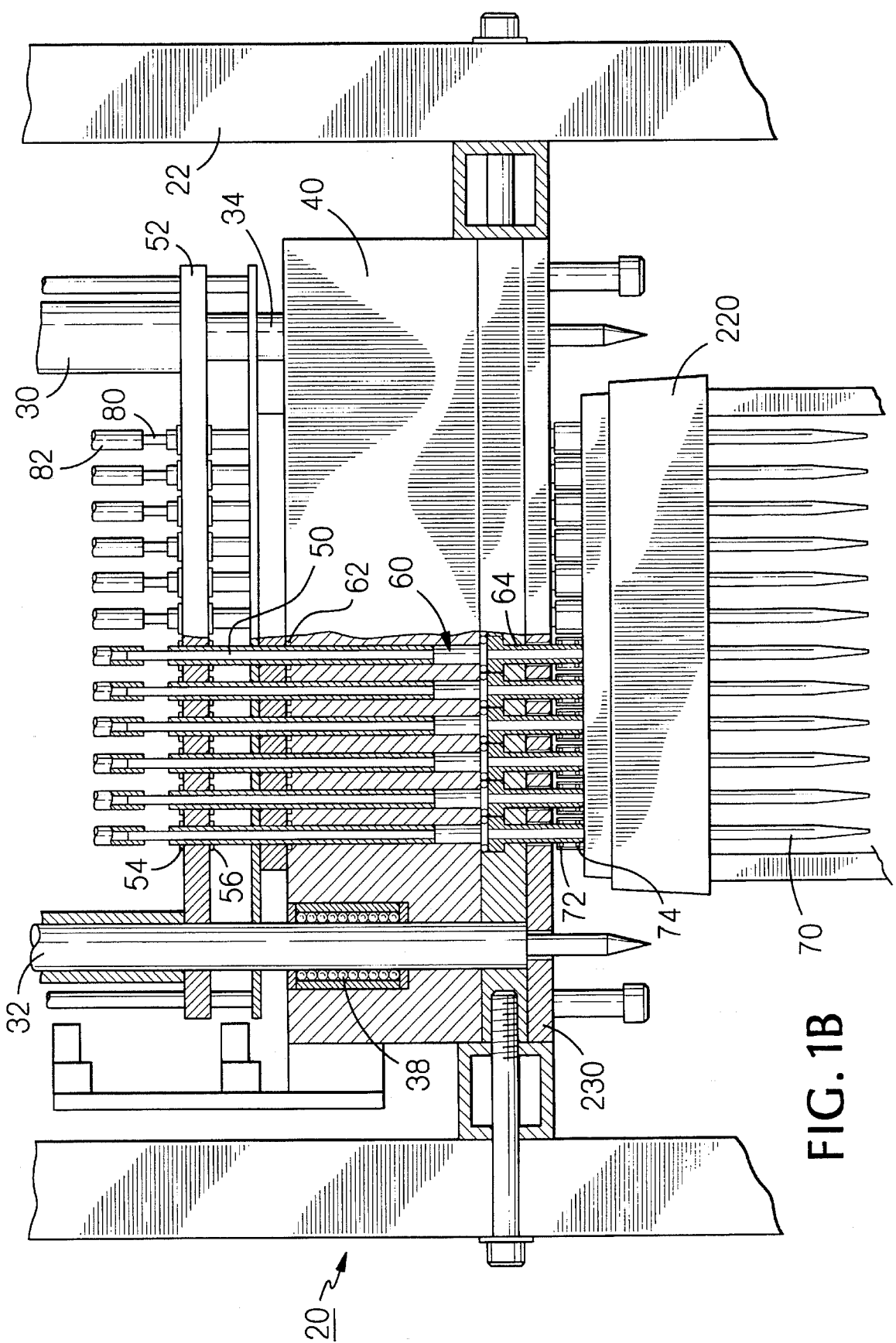
FIG. 1B is a fragmentary portion of FIG. 1, with some of the elements of the device in a different operating position.

Referring primarily now to FIGS. 1A and 1B, there is illustrated an automatic sample transfer device according to the present invention, generally indicated by the reference numeral 20.

Device 20 includes a frame 22, comprising several rigidly joined members, and a motor 24 fixedly mounted to the frame, which motor drives a lead screw 26.

A head carriage 30 engages lead screw 26, so that the head carriage may be raised and lowered by the rotation thereof, and the head carriage is guided by guide rods 32 and 34 which are fixedly attached to the head carriage and which are journalled in linear bearings, as at 36 and 38, fixedly attached, respectively, to the upper portion of frame 22 and to a head block 40 which is also fixedly attached to the frame.

Referring also to FIG. 5 in conjunction with FIG. 1B, device 20 includes 96 hollow tube pistons, as at 50, attached to a lift plate 52 which comprises the lower portion of head carriage 30 (FIG. 1B). Pistons 50 are attached to lift plate 52 by means of retainer rings, as at 54 and 56, so as to restrict vertical movement, but to allow some degree of lateral movement. This feature minimizes the need for precision clearances that would be required if pistons 50 were rigidly attached to lift plate 52. Pistons 50 fit into cylindrical channels, as at 60, formed in the rigidly mounted head block 40. Pistons 50 are sealed to the walls of cylindrical channels 60 by means of elastomeric O-rings, as at 62. At the lower end of cylindrical channels 60 in head block 40 are hollow cylindrical pin extensions, as at 64, sealed to head block 40 by means of O-rings, as at 66. Removably attached to the lower ends of pin extensions 64 are pipette tips, as at 70, which are frictionally removably attached to the pin extension by means of upper and lower O-rings, as at 72 and 74, respectively, lower O-ring 74 is designed to seal between pipette tip 70 and pin extension 64, while upper O-ring is spaced apart vertically from the lower O-ring to provide a second point for tip alignment the pin extension and to augment sealing.

Pistons 50 and channels 60 are laid out in a 8×12 configuration, on 9-mm centers, complementary to that of a standard 96-well laboratory tray.

At the tops of pistons 50 are attached hollow transition pieces, as at 80, to which are attached flexible silicon rubber tubes, as at 82, the other ends of the tubes being attached to an internal reservoir 180 (FIGS. 1A and 5).

It can be seen from FIG. 1A that rotation of lead screw 26 by motor 24 will cause lift plate 52 to move up and down vertically, thus, in turn, causing pistons 50 to move axially up and down in channels 60, increasing or decreasing the free volumes of the cylinders.

As will be evident from the following discussion, a number of the elements shown on FIG. 1A are shown to illustrate their general arrangement in device 20, although they all would not necessarily be present simultaneously and/or in the particular relative configurations shown.

Figure 2:
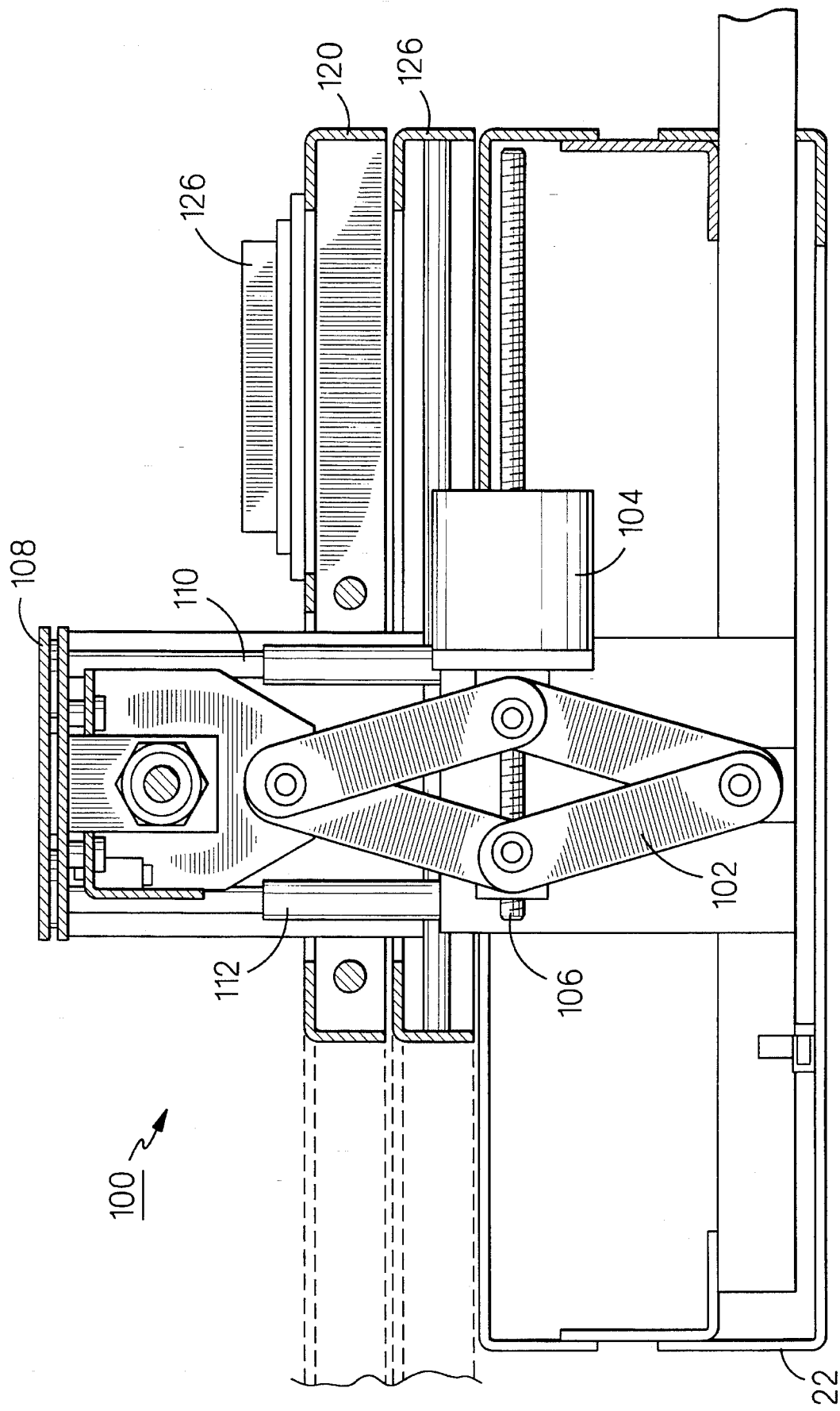
FIG. 2 is a side elevational view, partially in cross-section, of the means by which sample trays are raised and lowered in the device of FIG. 1.

Referring now to FIGS. 1A and 2, the mechanism by which a sample tray, such as sample tray 90 (FIG. 1A), may be raised to operating engagement with pipette tips 70 is generally indicated by the reference numeral 100. Mechanism 100 includes a scissors jack 102 fixedly mounted to frame 22 and driven between upper and lower positions (upper position shown) by means of an electric motor 104 (FIG. 2) and a lead screw 106. Slidingly mounted to the top of scissors jack 102 is a support platform 108. Support platform 108 is guided in its up and down vertical movement by means of four dowels, as at 110, journalled in guide tubes, as at 112. A touch off solenoid 114 (FIG. 1) is provided to cause a slight horizontal movement of support platform 108, the purpose of which will be described below.

Continuing to refer to FIGS. 1A and 2, mechanism 100 includes horizontally moveable upper and lower X-Y platforms 120 and 122, respectively, to selectively position additional sample trays such as sample tray 124 (FIG. 1A) and sample tray 126 (FIG. 2) such that they may be individually raised by scissors jack 102. As shown on FIG. 1A, upper X-Y platform 124 is moveable left and right and, as shown on FIG. 2, lower X-Y platform 126 is movable left and right. Thus, with scissors jack 102 lowered such that sample tray 90 is placed on upper X-Y platform 124 and such that support platform 108 is below lower X-Y platform 26, the upper X-Y platform may be moved, by manual or conventional mechanical means (not shown), one station to the right on FIG. 1A to place sample tray 124 over the support platform so that scissors jack 102 may be operated to place that sample tray in operating relationship with pipette tips 70 (FIG. 1A). Likewise, lower X-Y platform 26 may be moved one station to the left on FIG. 2 to place sample tray 126 over support platform.

Figure 4:
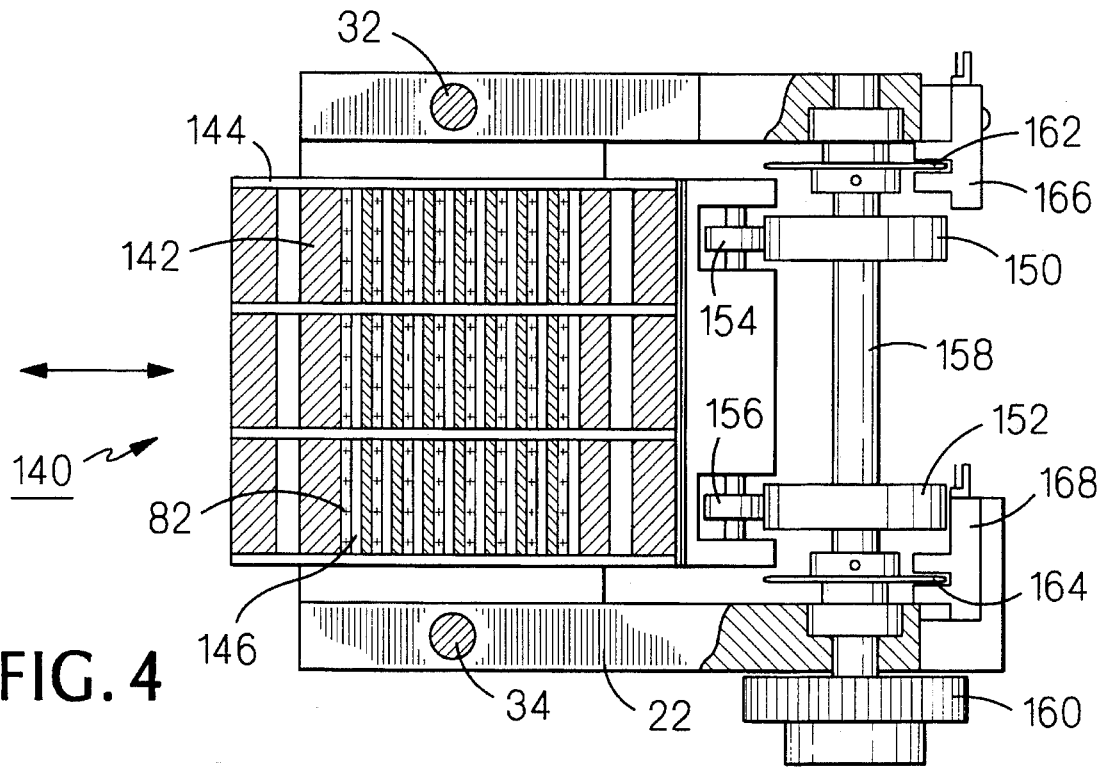
FIG. 4 is a plan view, partially in cross-section, taken along line "4—4" of FIG. 3.
Figure 3:
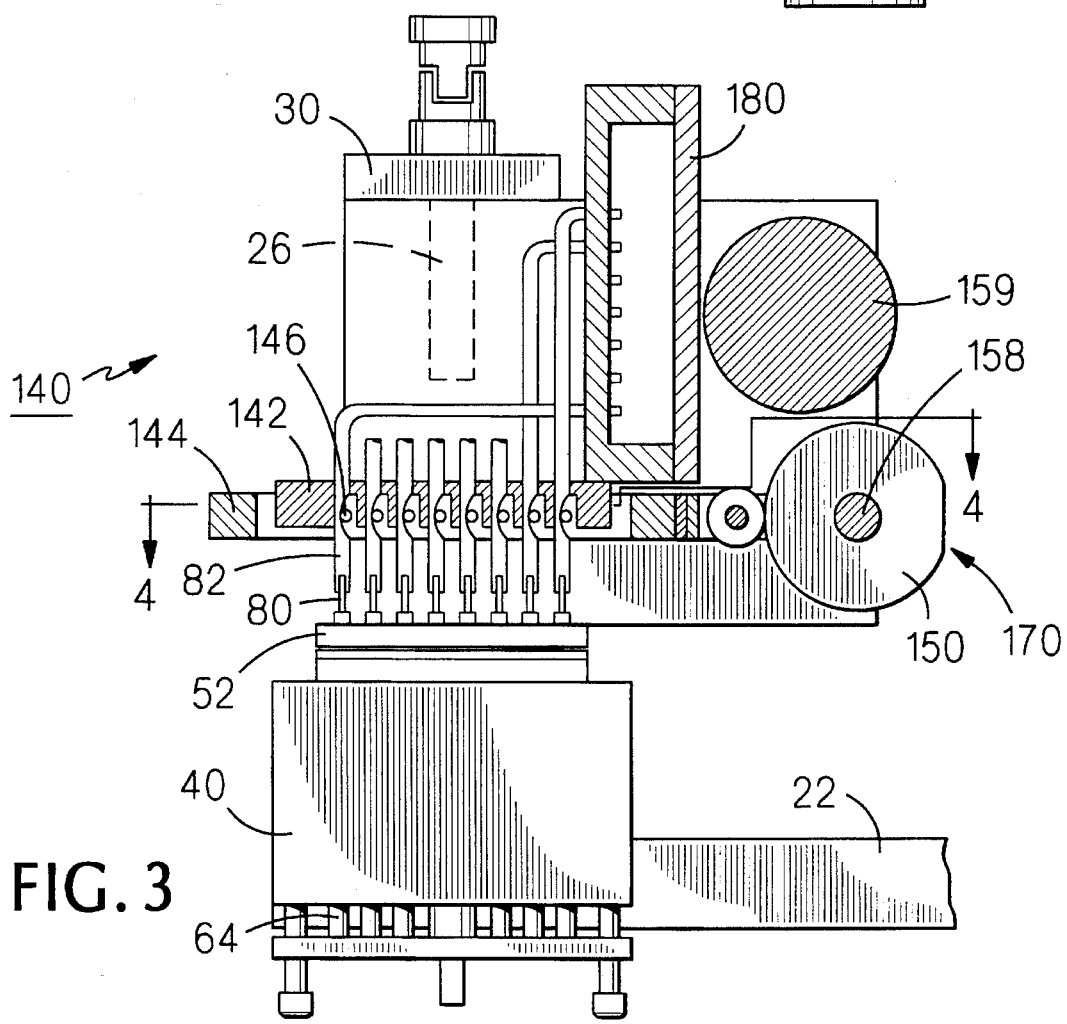
FIG. 3 is side elevational view, partially in cross-section, of the tube clamping portion of the device of FIG. 1.

Referring now to FIGS. 3 and 4, there is shown the mechanism by which tubes 82 may be selectively pinched to prevent fluid flow therethrough, the mechanism generally indicated by the reference numeral 140. Mechanism 140 includes an anvil 142 fixedly disposed with respect to frame 22 and a clamping frame 144 movable horizontally left and right on FIGS. 3 and 4. Clamping frame 144 includes eight clamping bars, as at 146, orthogonally disposed with respect to the direction of movement of clamping frame 144, each of which clamping bars is disposed to engage twelve of tubes 82 and clamp them against anvil 142 to thereby prevent fluid flow therethrough.

Tubes 82 are held in the clamped position shown by means of circular cams 150 and 152 engaging cam followers 154 and 156, respectively, the latter being journalled in clamping frame 144. Circular cams 150 and 152 are mounted on a rotatable shaft 158 which is journalled in frame 22 and rotated by an electric motor 159 (FIG. 3) through a gear train 160 (partially shown on FIG. 4). Also mounted on shaft 158 for rotation therewith are optical disks 162 and 164 cooperating with fixed optical sensors 166 and 168, respectively. When shaft 158 rotates such that flats on circular cams 150 and 152, such as flat 170 on circular cam 150 (FIG. 3), engage cam followers 154 and 156, the inherent resilience of silicon rubber tubes 82 will cause clamping frame 144 to move to the right and to open the tubes.

Reference now to FIGS. 5 and 6 will aid in understanding how device 10 operates to aspirate and discharge liquids through pipette tips 70. FIGS. 5 and 6 illustrate one pipette tip 70, one piston 50, and the elements associated therewith as described above with reference to FIGS. 1–4. Additionally, completing the fluid system of device 10, silicon rubber tube 82 is connected to an internal reservoir 180 (also FIG. 3) which is in turn connected to an external reservoir 182 through a line 184. External reservoir 182 has liquid fill, vacuum, vent, pressure, and drain lines attached thereto through controlled valves 186, 188, 190, 192, and 194, respectively.

One means of aspirating and dispensing liquids from and to sample tray 90 is to maintain tube 82 pinched between anvil 142 and rod 146 by operating clamp mechanism 140 as described with reference to FIGS. 3 and 4. Then, piston 50 is drawn up and down in cylindrical channel 60 by means of lift plate 52 being driven up and down by motor 24 (FIG. 1A), with the piston being raised to aspirate liquid into pipette tip 70 and being drawn lowered to dispense liquid from the pipette tip. By precisely controlling the rotation of motor 24, control is provided for aspirating or dispensing liquid into or from pipette tip 70, since the volume of liquid dispensed is directly proportional to the number of turns of motor 24.

It will be understood that, since all pistons 50, pipette tips 70, and the elements associated therewith are symmetrically disposed, and since all the pistons are similarly connected to lift plate 52, equal volumes of liquid will be aspirated into or dispensed from the pipette tips. Also, it will be understood that liquid may be aspirated from the wells on one sample tray and dispensed into the wells on another sample tray.

A second means by which liquid may be aspirated into or dispensed from pipette tips 70 is to leave pistons 50 in a fixed position. Now, clamp mechanism 140 (FIGS. 3 and 4) may be operated to permit liquid from external reservoir 182 to flow into the wells on sample tray 90. The length of time the clamp mechanism 140 is open and the pressure on the liquid in external reservoir 182 determine the amount of liquid that will be dispensed. The length of time clamp mechanism 140 is open is determined by the length of of flat 170 (FIG. 3) on circular cam 150 and the speed of rotation of the circular cam. Since the cam dimensions are fixed, the open time of clamp 140 is directly proportional to the speed of rotation of clamp motor 159, precisely controlling the speed of clamp motor 159 precisely controls clamp open time. If a fixed pressure is applied to external reservoir 182, the amount of liquid dispensed through pipette tips 70 will be directly proportional to the length of time clamp mechanism 140 is open. Again, since all fluid flow elements of device 10 are symmetrically disposed, equal volumes will be dispensed from pipette tips 70. This method of liquid dispensing is useful for rinsing sample wells while rinsing the entire liquid path of device 20.

If a vacuum is applied to external reservoir 182, liquid may be aspirated through pipette tips 70 to completely fill the system by leaving clamp mechanism 140 open for a period of time. When the liquid level begins to rise in external reservoir 182, clamp mechanism 140 is closed. By removing the vacuum and opening external reservoir 182 to the atmosphere, additional liquid can be added and the external reservoir closed and pressure applied. With the resulting totally filled (back filled) system, more precise volumes may be aspirated and dispensed.

With such a back filled system, aspirated and dispensed volumes can be more precisely controlled by the two methods described above. Pistons 50 can now operate in a positive displacement mode as opposed to an air displacement mode, since the spaces between the pistons and pipette tips 70 are filled with an incompressible liquid, such as water, instead of a compressible gas (air).

Referring now to FIG. 6, which illustrates one pipette tip 70 operated in a liquid filled mode, it is shown that sample liquid 200 can be separated from piston liquid 202 by aspirating a small air gap 204 into the tip orifice of pipette tip 70 before aspirating the sample liquid. As is further seen on FIG. 6, pipette tip 70 includes an upper portion 210 which provides an internal volume for holding liquid and a lower portion 212 which is much narrower than the upper portion and which is essentially straight except at the tip orifice. This configuration of lower portion 212 allows the use of air gap 204 to separate liquids as described above.

FIGS. 7(A)–7(F) illustrate how pipette tip 70 is mounted, used, and removed.

Figure 7:
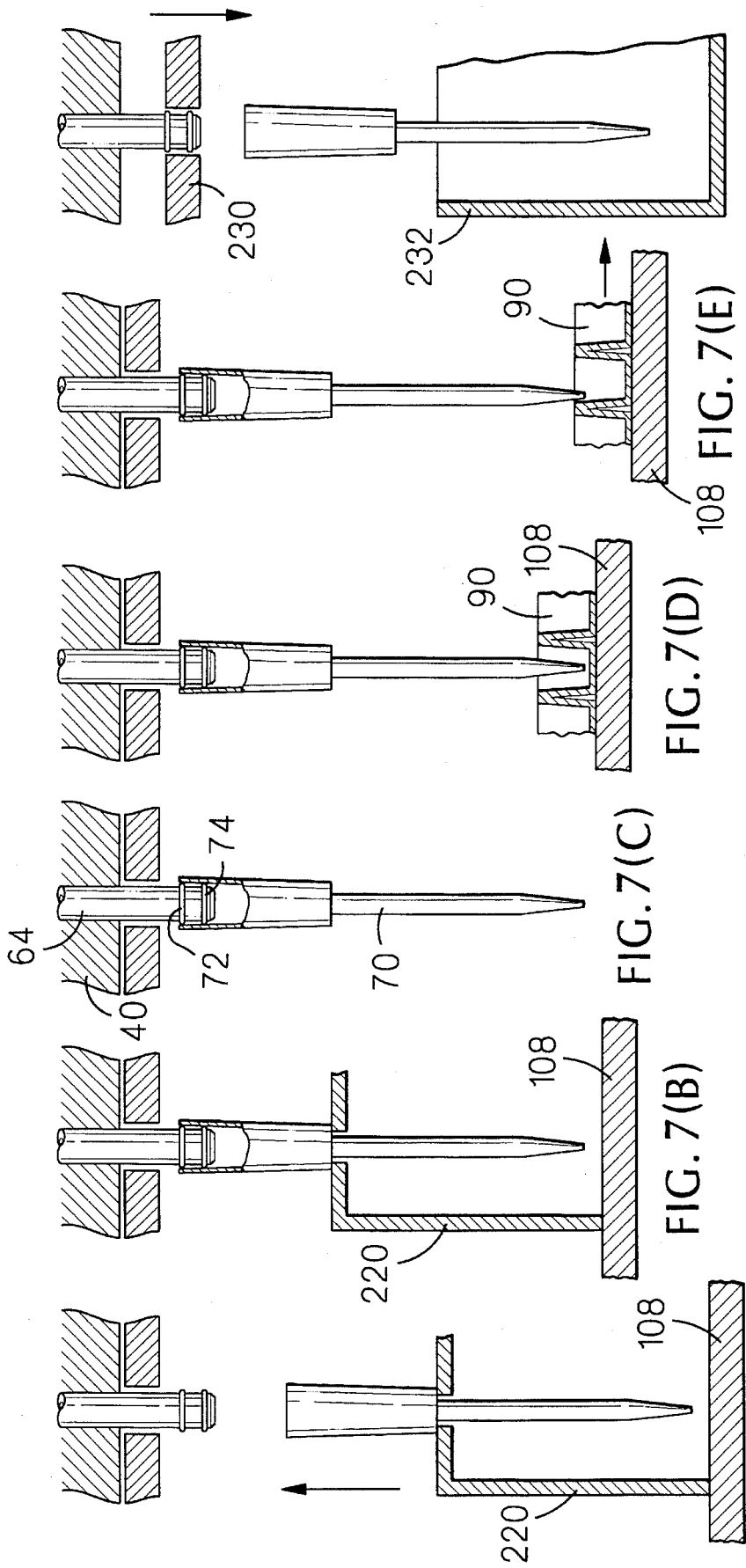
FIGS. 7(A)–(F) are enlarged, side elevational views partially in cross-section, illustrating how the tip of FIG. 6 is used with the device of FIG. 1, including the mounting and ejecting of the tip.

It is desirable to load and unload all 96 pipette tips 70 automatically and simultaneously. A loading fixture 220 is provided into which all pipette tips 70 are inserted (FIG. 7A–also FIGS. 1A and 1B). It will be understood that pipette tips 70 are disposed in fixture 220 in the same pattern as pin extensions 64. Loading fixture 220 is placed on support plate 108 and scissors jack 102 (FIGS. 1A and 2) is operated to raise the loading fixture so that the upper ends of pipette tips 70 engage pin extensions 64 and to force the pipette tips onto the pin extensions. Scissors jack 102 provides the desired mechanical advantage to perform this operation, since maximum force is desired at this point and provided by the scissors jack, while at the lower end of travel of the scissors jack, the scissors jack provides minimum force but fast travel which is desired at that point. To minimize the force required to fit and seal 96 pipette tips 70 simultaneously, lower O-ring 74 is sized to be slightly smaller in outside diameter than the inside diameter of the top of the pipette tip to allow easy entry of pin extension 64 into the tip. As the top of pipette tip 70 is pushed onto pin extension 64, the normal draft used in the molding process to form tip 70 allows lower O-ring 74 to seal to the inside diameter of the top of pipette tip 70. As the sealing interference occurs, upper O-ring 72 enters the top of pipette tip 70 to hold it in vertical alignment on extension pin 64 and to provide an additional sealing point.

After pipette tips 70 have been mounted as described above, scissors jack 102 is lowered (FIG. 7C) and then sample tray 90 raised into operating engagement with the lower ends of pipette tips 70 (FIG. 7D) and the aspirating and/or dispensing procedures described above conducted.

When delivering small liquid volumes, such as 10 microliters, it may be necessary to "touch off" the tips of pipette tips 70 to remove the small volumes. This may be accomplished by touching the liquid surface or by touching the sidewalls of the receiving receptacle. If the orifice end of pipette tip 70 is not to be contaminated by the liquid in sample tray 90, then the sidewall must be used for touching off as is shown in FIG. 7E. Here, support plate 108 has been shifted slightly in the direction of the arrow so that the tip of pipette tip 70 is just touching a sidewall in sample tray 90. The means by which this shifting is accomplished is energization of touch off solenoid 114 (FIG. 1A) which shifts support plate 108 to the right. Support plate 108 is biased to its normal operating position (FIG. 7D) by means of a spring 115 (FIG. 1A).

When it is desired to remove pipette tips 70, a stripper plate 230 is lowered (FIG. 7F) to press against the tops of the pipette tips, thus forcing the pipette tips off the pin extensions 64. The removed pipette tips 70 may fall into a receptacle 132 provided for that purpose.

Reference should be made back to FIGS. 1A and 1B for a detailed understanding of the means by which stripper plate 230 is lowered. FIG. 1B illustrates device 20 with the moving elements thereof related to pipette tips 70 as they would be disposed after installation fixture 220 has been used to install the pipette tips in place, as is shown in more detail on FIG. 7B. It will be understood that the operations shown on FIGS. 7D–7F will follow in sequence. It is to be noted from FIG. 1B that lift plate 52 is spaced above the top of head block 40 and stripper plate 230 is located just at the top of pipette tips 70. In this position, head carriage 30 has been lowered to its lowest operating position; that is, when device 20 is used in the displacement mode, the positions of pistons 50 shown will be the lowest discharge position, having been moved to that position by the lowering of the head carriage. Further downward movement of head carriage 30 will cause stripper plate to move to the position shown on FIG. 1A to remove pipette tips 70 as shown on FIG. 7F. At this point, lift plate 52 has engaged the top of head block 40.

As indicated above, some elements, such as the lowered position of stripper plate 230, are included for general reference only, and pipette tips 70 would not be ejected while installation fixture 220 and sample tray 90 were in the positions shown. Likewise, installation fixture 220 and sample tray 90 would not simultaneously be in the positions shown. Also, in spite of stripper plate 230 being shown in its lowered position, pipette tips 70 are shown (cut away portion of the stripper plate) as being installed in operating position.

It will be understood that the various operations indicated on FIGS. 7(A)–7(E) may be carried out with the aid of having mounting fixture 220, one or more sample trays 90, and receptacle 232 positioned on upper X-Y platform 120 (FIGS. 1A and 2) and manually or automatically indexing these over support plate 108 as needed. The latter operation, as well as other functions of device 10, may be accomplished through the use of a programmable computer having programmed sequences retained in a non-volatile memory for recall and use. The logical sequence is determined by the testing protocol and can be easily set by the user. This is accomplished by providing a menu of the available functions for each cycle which are also available on repeated cycles. A function may be selected, or not, on each cycle, thereby allowing a complete series of functions to occur in an organized program. A typical menu of function for a given cycle may be as follows:

| | |
|---|---|
| Pick Up Pipette Tips | Yes - No |
| Station Number | 1,2 3,4 |
| Aspirate - Dispense | A/D |
| Volume | microliters |
| Stage Height | inches |
| Aspirate - Dispense | A/D |
| Volume | microliters |
| Mix Cycles | 1 thru 10 |
| Remove Tips | Yes - No |

Figure 8:
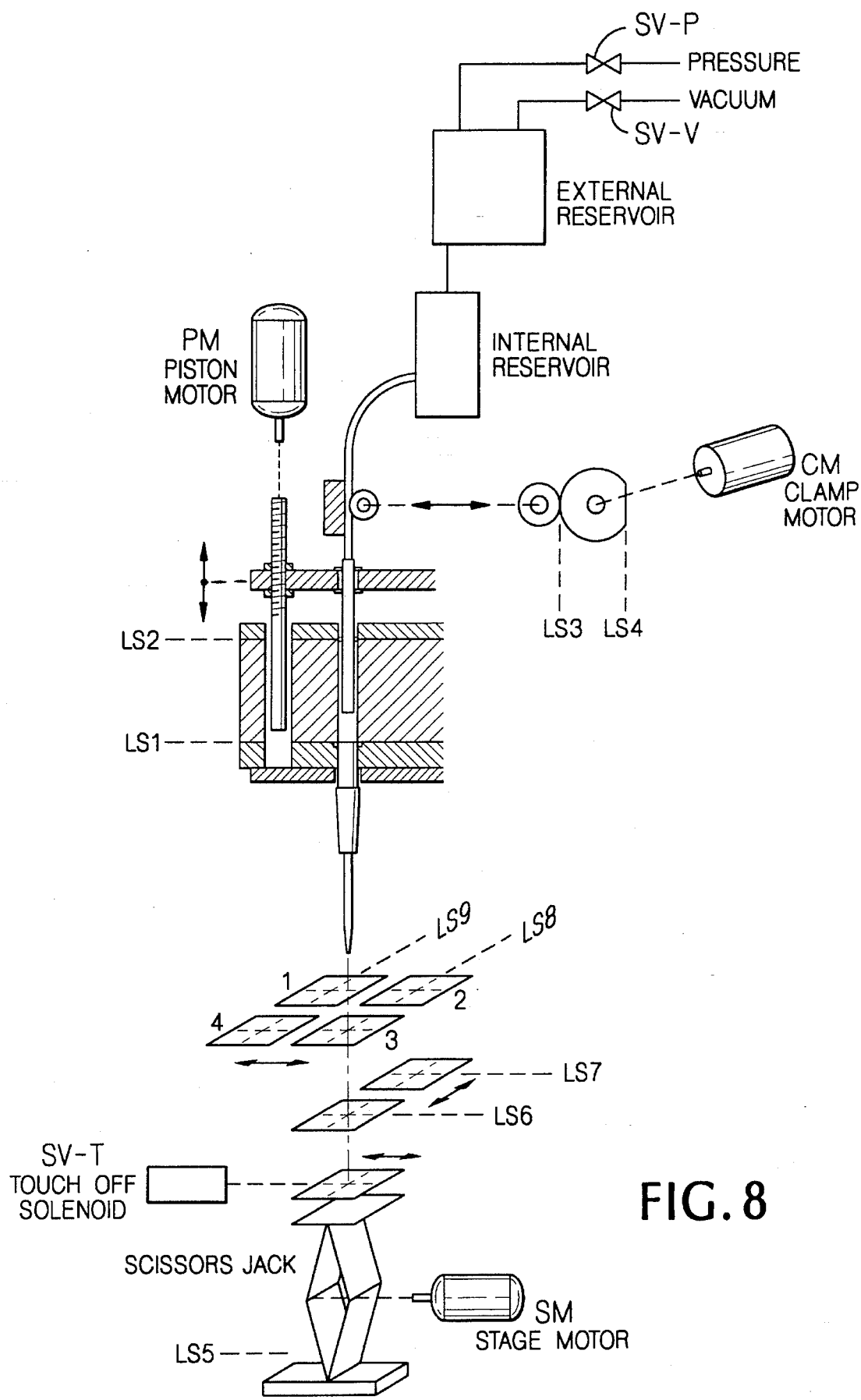
FIG. 8 is a schematic view illustrating the location and operation of the control elements of the device of FIG. 1.
Figure 9:
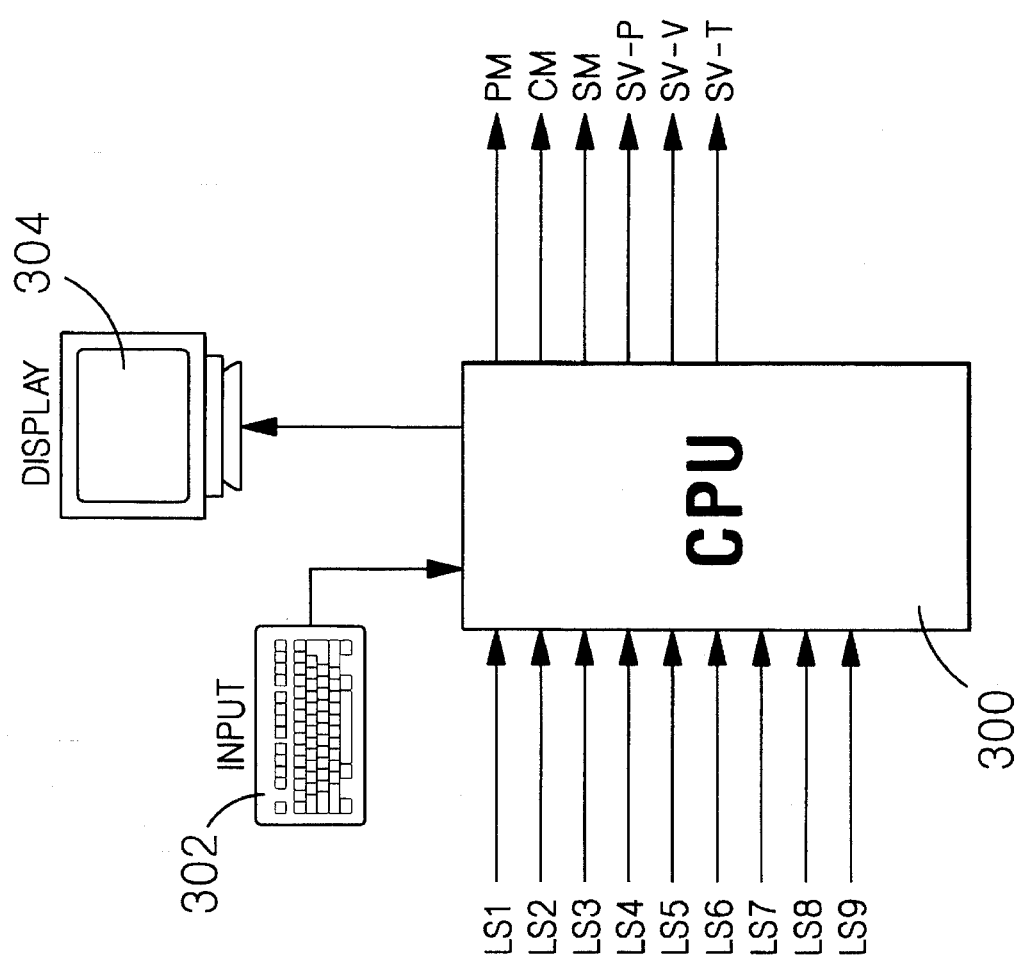
FIG. 9 is a block diagram of the controller components receiving inputs from, and providing outputs to, the control elements of FIG. 8.

Reference should now be made to FIGS. 8 and 9 in connection with the following description of system components and operation. FIG. 8 illustrates schematically the arrangement of the control elements of device 10, the physical arrangement of which has been described above. FIG. 9 is a block diagram of the control system and includes a central processing unit (cpu), or microprocessor, 300 which receives inputs from light switches LS1–LS9 and provides outputs to motors PM, CM, and SM and valves SV-P, SV-V, and SV-T. CPU 300 is programmed by, and receives additional commands from, an input keyboard 302 and provides status and other information on display 304. PM—Piston Motor Rapidsyn 34D9209. 200 steps/revolution.

Rated current: 4.6 amps
Rated Voltage: 2.5 vdc
Resistance/phase: 0.55 ohms
Gear In—Direct connected to a 0.100 inch/rev lead screw=10 revolutions per inch of head travel=0.3058 microliters per step
Maximum Total Travel=2.5 inches
Normal Volume Travel=0.817 inches for 500 ul
Distance to Eject Tips=0.50 inches CM—Clamp Motor Pittman 14000 motor 19.1 volt winding Mounted on a GM 14603 planetary gear head 75.11:1 Ratio Motor torque constant=7.41 oz.in./amp Gear Box 51% efficient Estimated gear head speed at 50 in #torque load at 24 volt DC=41.6 rpm Cam Gear in 30T to 50T or reversed=2.40 or 0.865 sec/rev SM—Stage Motor 23E Stepper Motor 200 steps/rev geared into the scissor jack with a 16 threads/inch acme screw
Total jack travel requires 42-½ revolutions of the stepper, i.e. 8496 steps AC—Air Compressor As required (not shown)

SV-V Vacuum Valve
Clippard 24 vdc, three way. When energized this valve connects the vacuum side of the compressor to the external reservoir. When deenergized it vents the vacuum source and closes to the external reservoir.

SV-P Pressure Valve
Clippard 24 vdc, three way. When energized it connects the pressure side of the compressor to the reservoir. When deenergized it vents the pressure side of the compressor.

SV-T Touch off Solenoid
Ledex #174412-028 rated 24 vdc, 28 awg, 16.9 ohms@20§C

The following light switches detect the stated conditions:
LS-1 Normally blocked, sees light when the piston head is in its low home position
LS-2 Normally blocked, sees light when the piston head is in its high limit position
LS-3 Normally blocked, sees light when the clamp cam is in its closed or home position
LS-4 Normally blocked, sees light when the clamp cam is in its open position
LS-5 Normally blocked, sees light when the stage is in its lowest or home position
LS-6 Normally blocked, sees light when the plate shuttle is in position #1 for tip pickup
LS-7 Normally blocked, sees light when the plate shuttle is in position #2 for tip eject
LS-8 Normally blocked, sees light when the plate shuttle is in position #3
LS-9 Normally blocked, sees light when the plate shuttle is in position #4

1.0 Initialization
Whenever the power is first applied, the cpu will run all motions under its control to a known position. The sequence is as follows. (The display will show "Initialization" except as noted.)

1.1 The clamp motor CM will move to close the clamp if LS-3 is not open. This will stop any flow coming from the reservoir.

1.2 If LS-5 is not open, then SM will run the stage down until it is open.

1.3 If LS-7 is not open, the display will prompt the operator "Move to Tip Discard". When the operator has complied, and LS-7 is open, the sequence continues.

1.4 The piston motor PM runs down until LS-1 opens. If LS-1 does not open within 1000 steps, the piston motor will reverse and run up until LS-1 opens.

1.5 If the piston motor PM was stopped going down by LS-1 in 1.4 above, it will now step down 1000 steps to eject any tips left on the head. PM will then reverse and step up until LS-1 again opens. If in 1.41 (above) PM stepped all the way down (1000 steps), then the tips, if any, were ejected at that point and 1.5 is not required.

1.6 The initialization is complete with the following conditions satisfied:
A—Clamp closed, LS-3 open
B—Stage lowered and home, LS-5 open
C—Tips ejected and pistons in low home position, LS-1 open
D—Plate shuttle is tip eject station, LS-7 open The display will now show "SST-96 Ready". Instrument is ready for operation in any of the following functions, as called for by the program.

2.0 Tip Pickup
When the tip pickup function is called for by the program, the following sequence of events occurs.

2.1 The display reads "Shuttle to Tip Pickup". If LS-6 is not open, the operator must move the shuttle to the tip pickup station. When LS-6 opens, the cpu will pause 1 second to allow for settling. It is assumed the operator has placed a rack of tips on the shuttle. If not, the operator can press STOP to halt operation. The display will show "Paused". Operation may be resumed by pressing RUN. It will proceed from the point the cycle was stopped.

2.2 After the 1 second delay, and with LS-6 open, the stage motor elevates 8500 steps to seat the tips on the head. It is assumed that the pistons are in their home position (LS-1 open) from the previous operation, either initialization or a tip eject cycle. During this time the display will show "loading Tips".

2.3 After elevating up 8500 steps, the stage motor SM reverses, and lowers the stage until it is in its home position, with LS-5 open.

2.4 With the stage lowered and LS-5 open, the tip load cycle is complete and released to the next sequence called for. The display is released to show the next instruction.

3.0 Aspirate Sample with Pistons
The following sequence occurs whenever it is desired to aspirate a sample by means of the pistons.

3.1 The display will prompt for the position of the plate shuttle with "Move Shuttle to #_____", as called for by the program.

3.2 When the appropriate LS is open, indicating the shuttle is in position, there is a 1 second settling time prior to the following sequence. As before, the operator may press STOP to cause the cycle to pause. It will resume when RUN is pressed.

3.3 If an air gap aspirate is called #or by the program, the piston motor (PM) will move the pistons up to aspirate the designated volume. This is used to aspirate an air gap prior to raising the sample on the stage. The up steps taken are retained in the air gap file for this sample.

3.4 The stage (SM) elevates to the position indicated by the program.

3.5 The piston motor (PM) raises the head the number of steps called for by the programs aspirate volume.

3.6 The stage lowers _____ steps to remove the tips from the liquid surface.

3.7 The touch off solenoid (SV-T) is energized for 1 second to touch off the tips against the receptacle side walls (if present).

3.8 The stage motor(SM) lowers until LS-5 opens, which completes the aspirate cycle. The display is released for the next sequence called for by the program.

4.0 Dispense Sample with Pistons

The following sequence occurs whenever a dispense cycle is called for using the pistons.

4.1 The display will prompt for the position of the plate shuttle with "Move Shuttle to #_____" as called for by the program.

4.2 When the appropriate LS closes, there is a 1 second pause for settling. The cycle may be paused as before by pressing STOP.

4.3 The stage motor (SM) will lift the stage to the appropriate setting called for by the program.

4.4 The piston motor (PM) will run down to dispense the desired volume. The aspirate/dispense volume file must be accessed by the cpu to determine if a previous sample's air gap must be dispensed prior to dispensing the program volume. On any change of direction of the piston motor, the appropriate steps must be taken to compensate for backlash.

4.5 SV-T is energized for 1 second to touch off the tips.

4.6 The stage motor (SM) returns the stage to its lowest home position when LS-5 opens. This completes the dispense cycle, and releases the display for the next sequence.

5.0 Mix Cycles

A dispense cycle may be followed with several mix cycles to mix the contents of the receiving receptacle by successive aspirate and dispense cycles.

5.1 Following a dispense, the program may call for mixing. This would occur after 4.4 in the dispense cycle. The piston motor (PM) would reverse and run up, aspirating the volume called for in the mix cycle program parameter.

5.2 Upon completion of the aspirate, the piston motor (PM) will reverse, and run down, dispensing the same volume as was aspirated.

5.3 The aspirate and dispense cycles of 5.1 and 5.2 are repeated the required number of times, as determined by the program parameters. On each change of direction PM must compensate for backlash, using the preset backlash parameter.

5.4 At the completion of the mix sequence, the program returns to 4.5 of the dispense cycle.

6.0 Tip Removal 6.1 The display will prompt "Tip Eject". The operator must move the shuttle to that position, which opens LS-7. When LS-7 opens, it initiates the following sequence.

6.2 After a 1 second delay for settling, the piston motor (PM) will run down to its lower home position, where LS-1 opens. It then proceeds on down the required number of steps, as set by the tip eject parameter. This will force the tips off the head into the waiting receptacle. The piston motor (PM) reverses, and runs up until it reaches its home position, as confirmed by LS-1 opening again.

7.0 General Controls

The following control comments apply:

7.1 The automatic cycle can be stopped at anytime by pressing the STOP push button. Pressing RUN will restart the program from where it stopped. The display will show "Paused" during the stopped period. There are several functions that would complete their action prior to stopping. They are as follows:

7.11 The clamp motor will only stop at two points, as determined by the program. Either the clamp open (LS-4 open) or with the clamp closed (LS-3 open).

7.12 The touch off solenoid will remain on for 1 second after it is initiated.

7.2 The piston motor (PM) must compensate for system backlash on every reversal of direction. The backlash parameter should be adjustable through the set-up mode for each instrument.

7.3 An up/down count register of piston motor steps should be maintained to accomplish the following:

7.31 An aspirate volume must always proceed the first dispense volume 7.32 A programmed dispense volume cannot exceed the previous aspirate volumes.

7.33 A mix cycle cannot be executed unless the total volume aspirated has been dispensed.

7.34 The total aspirate volume within the tip (register) cannot exceed 500 ul at any time.

7.35 Where an air gap is used to separate reagents, the total aspirated volume on that sequence cannot exceed 100 ul, the volume of the tip barrel.

7.36 When dispensing a volume with an associated air gap, the volume is dispensed and followed by its associated air gap.

8.0 Backfilling the System

The following sequence of events is initiated to back fill the system with liquid. It is achieved by pressing the FUNCTION push button and scrolling the PROGRAM buttons to "Back Fill System". Pressing RUN initiates the following sequence:

8.1 The air compressor is started 8.2 The vacuum valve (SV-V) is energized, connecting the vacuum side of the compressor to the inlet of the reservoir. SV-P is deenergized, venting the inlet side of the compressor to atmosphere.

8.3 After a 5 second time delay to allow vacuum buildup, the clamp motor (CM) turns to open the clamp (LS-4 open). With the tips submerged in liquid, the system will begin to backfill.

8.4 The operator stops the backfill process by pressing STOP to initiate the following sequence:

8.41 Clamp motor (CM) turns to close the clamp (LS-3 opens) stopping CM 8.42 The air compressor stops and SV-V is deenergized.

9.0 Time/Pressure Dispense Cycles

Time pressure delivery cycles are used for washing out the tips, and for rapidly delivering the same volume of a common reagent to a number of plates. They are selected by pressing the FUNCTION push button, then using the PROGRAM push buttons to scroll through the following operating modes:

Wash Tips

Timed Delivery 1

Timed Delivery 2

Timed Delivery 3

Timed delivery 4

Pressing the SELECT button selects the desired operating mode. The display flashes to indicate that mode has been selected, and a timed dispense will be initiated when the RUN button is pressed.

The timed pressure cycles are preset by the operator (see Programming). Any time a timed pressure mode has been selected the air compressor turns on and continues to run as long as the menu is selected. SV-P is energized to connect air pressure to the reservoir. Pressing RUN after the mode has been selected initiates the following sequence:

9.1 Tip Wash Out
   9.11 For this program to operate the shuttle must be in the tip eject position (LS-7 is open). It is assumed the operator has placed a receiving pan at this location to catch the effluent.
   9.12 The air compressor must run 10 seconds after it has been started before any time-pressure sequence can occur. When this timer times out, pressing the RUN initiates the following:
   9.13 Clamp Motor (CM) turns until LS-4 opens, indicating the clamp is open. CM stops, leaving LS-4 open until the time set in the program has elapsed.
   9.14 When the set time has elapsed, the clamp motor (CM) turns until stopped by LS-3 opening, which leaves the clamp in the closed position.

9.2 Timed Pressure Dispenses
   For timed pressure dispenses, the program will set the shuttle position stage height and volume dispensed. The volume dispensed is determined by the number of revolutions the cam makes to open the clamp. On each opening, a preset volume is delivered as determined by head pressure and clamp motor speed. The total volume delivered is an accumulation of the set increments on each revolution.
   9.21 If the shuttle is not in the position selected by the program when the RUN push button is pressed, the display will switch from flashing "Timed Delivery__ __" to a prompt message "Shuttle to Position__ __".
   9.22 When the appropriate LS is open, indicating the shuttle is in the selected position, the stage motor(SM) will lift the stage to its set value, as determined by the program.
   9.23 After the stage motor stops, indicating the stage is in position, the RUN push button is enabled. The display will flash "Timed Delivery X".
   9.24 Pressing RUN will execute the number of clamp openings called for by the program. The clamp motor will run to open LS-4 the required times, then stop with the clamp closed, LS-3 open.

10.0 Programming
   A program Piston Displacement Mode, other than the time dispense programs, is established by linking together several cycles. Up to 10 cycles can be linked in one program. Up to 10 programs can be retained in memory. Each cycle can control the following parameters. To bypass a parameter, it is set to zero.

| Pick up Tips | Yes No |
| --- | --- |
| Aspirate Air Gap | __ __ volume, in ul |
| Station Number | 1 2 3 4 |
| Stage Height | _. __ __ __ , inches |
| Aspirate or Dispense | A/D |
| Volume | _, microliters |
| Mix | Yes/No |
| Mix Cycles | _ |
| Mix Volume microliters | __ __ __, |
| Wash Tips | Yes/No |
| Eject Tips | Yes/No |
| Pause | Yes/No |

10.1 When running a program, the cpu looks ahead at the next cycle. If the same station is selected for the next cycle, the stage only lowers 0.75 inches to allow removal of the plate. It then returns to the height set by the next cycle. This will minimize cycle time, where the same station is used for repeated aspirates or dispenses. If another station has been selected for the next cycle, the stage motor must run down to its home position (LS-5 open) to allow the shuttle to be moved by the operator. This would occur after the mix portion of the cycle. When the shuttle is in position for the next cycle, the stage rises to the set height enabling the next cycle.
   10.2 An LED lights to indicate the station in the next cycle. The LEDs will change status after the aspirate or dispense cycle has started.

11.0 Programming Time Pressure Mode
   There are five programs that may be set in the timed pressure mode. They are:
   Wash Tips
   Timed Delivery #1
   Timed Delivery #2
   Timed Delivery #3
   Timed Delivery #4

To program these modes, press the FUNCTION push button, then scroll to the desired program, using the PROGRAM push button. Press SET UP push button to enter the set-up mode. Use the cursor buttons to select the following parameters, and the VALUE button to change them.
   11.1 Wash Tips Station #2 is automatically selected. The stage height is fixed at its home position (LS-5 open).
      11.12 Set length of time the clamp is to be open in 0.1 second increments
   11.2 Timed Delivery #1, #2, #3, #4
      11.21 Select Station Number 1, 2, 3, or 4
      11.22 Select Stage Height ___.___ ___ ___ inches
      11.23 Select number of pulses revolutions) the clamp motor is to make 12.0 Miscellaneous Control Functions
   12.1 If, in a given program, the wash tip feature is selected, then the air compressor comes on when that program is selected. It stays on until the program is exited. Concurrently SV-P is energized to apply pressure to the reagent reservoir.

Except for the elements of the invention indicated above as being constructed from polymeric materials, the other major elements of the invention may be economically constructed from any suitable materials by conventional methods and, particularly the liquid contacting elements, may be constructed of stainless steel for ease of cleaning and to minimize corrosion.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A device for selectively dispensing or aspirating a plurality of liquid samples to or from a plurality of sample wells, comprising:

(a) a plurality of parallel channel means having first and second ends lying in first and second common planes;

(b) a plurality of hollow piston means having first and second ends, with said second ends thereof being disposed within said channel means for relative axial movement between said first and second ends of said channel means;

(c) a plurality of fluid sealing means disposed between said piston means and said first ends of said channel means;

(d) a plurality of pipette tips disposed at said second ends of said channel means;

(e) a plurality of tube means having first and second ends, with said second ends thereof being operatively attached to said first ends of said piston means;

(f) reservoir means to which said first ends of said tube means are attached;

(g) flow stopping means disposed between said first and second ends of said tube means to selectively stop fluid flow through said tube means;

(h) means operatively attached to said piston means to selectively simultaneously raise or lower said second ends of said piston means within said channel means; and (i) means to fill said device with liquid, so that at least said pipette tips, said channel means, said hollow piston means, and said tube means between said first ends of said piston means and said flow stopping means are substantially filled with said liquid;

such that, when said device is so filled with liquid and said flow stopping means is operated to stop liquid flow through said tube means, raising or lowering said piston means within said channel means will aspirate liquid into or dispense liquid from said pipette tips;

and said device further comprising:

(j) means to selectively apply vacuum or pressure to said reservoir means;

such that, when said flow stopping means is operated to permit fluid flow through said tube means, selectively applying vacuum or pressure to said reservoir means will aspirate liquid into or dispense liquid from said pipette tips.

2. A device, as defined in claim 1, further including programmable means to control said flow stopping means and said means operatively attached to said piston means.

3. A device, as defined in claim 1, wherein said plurality of tube means are flexible tubes and said flow stopping means selectively stops said fluid flow through said flexible tubes by simultaneously pinching together the walls of each of said tubes.

4. A device, as defined in claim 3, wherein said said flow stopping means comprises:

(a) a fixed anvil against a surface of which said flexible tubes are disposed;

(b) a clamping frame engagable with said flexible tubes and selectively movable between a first position near said surface so as to pinch said flexible tubes and a second position away from said surface so as to permit said tubes to become unpinched and allow fluid flow therethrough; and (c) operating means to move said clamping frame between said first and second positions.

5. A device, as defined in claim 4, wherein said operating means includes a rotating circular cam engaging a cam follower operatively connected to said clamping frame, said circular cam having defined in the periphery thereof a flat, such that, when said flat engages said cam follower, said clamping frame will move to said second position, and, when said flat does not engage said cam follower, said clamping frame will move to said first position; whereby, controlling the rate of rotation of said cam will control the length of time, and the intervals between the times, said tubes are unpinched.

6. A method of selectively dispensing or aspirating a plurality of liquid samples to or from a plurality of sample wells, comprising:

(a) providing a plurality of parallel channel means having first and second ends lying in first and second common planes;

(b) providing a plurality of hollow piston means having first and second ends, with said second ends thereof being disposed within said channel means for relative axial movement between said first and second ends of said channel means;

(c) providing a plurality of fluid sealing means disposed between said piston means and said first ends of said channel means;

(d) providing a plurality of pipette tips disposed at said second ends of said channel means;

(e) providing a plurality of tube means having first and second ends, with said second ends thereof being operatively attached to said first ends of said piston means;

(f) providing reservoir means to which said first ends of said tube means are attached;

(g) providing flow stopping means disposed between said first and second ends of said tube means to selectively stop fluid flow through said tube means;

(h) providing means operatively attached to said piston means to selectively simultaneously raise or lower said second ends of said piston means within said channel means; and (i) selectively either:
(i) operating said flow stopping means to stop fluid flow through said tube means; and
(ii) raising or lowering said piston means within said channel means to aspirate liquid into or to dispense liquid from said pipette tips;

or (iii) operating said flow stopping means to permit fluid flow through said tube means; and
(iv) selectively applying vacuum or pressure to said reservoir means to aspirate liquid into or to dispense liquid from said pipette tips.

7. A method as defined in claim 6, further comprising the steps of:

(j) inserting said pipette tips into liquid containing means;

(k) operating said flow stopping means to permit flow through said tube means;

(l) applying vacuum to said reservoir means so as to draw liquid into said pipette tips, said tip attachment means, said channels, said hollow pistons, and said tube means to said reservoir means; and (m) selectively either:
(i) operating said flow stopping means to stop fluid flow through said tube means; and
(ii) raising or lowering said piston means within said channel means to aspirate liquid into or to dispense liquid from said pipette tips;

or (iii) operating said flow stopping means to permit fluid flow through said tube means; and
(iv) selectively applying vacuum or pressure to said reservoir means to aspirate liquid into or to dispense liquid from said pipette tips.

8. A method, as defined in claim 7, wherein the steps of said method include the step of tip ejection.

9. A method, as defined in claim 6, further comprising providing programmable means to automatically control the steps of said method.

10. A method, as defined in claim 6, further comprising the step of:

(n) periodically operating said flow stopping means to permit fluid flow through said tube means for a set period of time while applying a given pressure or vacuum to said reservoir means, so as to control the quantity of fluid passing through said tube means during said period of time.

* * * * *